United States Patent
Krueger et al.

(10) Patent No.: US 7,285,117 B2
(45) Date of Patent: Oct. 23, 2007

(54) MEDICAL DEVICE CONTROL SYSTEMS

(75) Inventors: Katie L. Krueger, San Jose, CA (US); Jon Wohlgemuth, Morgan Hill, CA (US); Robert F. Bencini, Sunnyvale, CA (US); Miriam H. Taimisto, San Jose, CA (US); Richard Lardner, Oakland, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 947 days.

(21) Appl. No.: 10/098,661

(22) Filed: Mar. 15, 2002

(65) Prior Publication Data

US 2003/0176778 A1   Sep. 18, 2003

(51) Int. Cl.
 *A61B 18/14* (2006.01)
 *A61B 5/04* (2006.01)
(52) U.S. Cl. .................... 606/34; 606/41; 606/42; 600/374
(58) Field of Classification Search ............ 606/34–42; 128/899
 See application file for complete search history.

(56) References Cited

U.S. PATENT DOCUMENTS

| | | | |
|---|---|---|---|
| 4,170,234 A * | 10/1979 | Graham | ................. 606/42 |
| 5,131,397 A | 7/1992 | Crowley | |
| 5,972,012 A | 10/1999 | Ream et al. | |
| 6,004,269 A | 12/1999 | Crowley et al. | |
| 6,064,902 A | 5/2000 | Haissaguerre et al. | |
| 6,142,994 A | 11/2000 | Swanson et al. | |
| 6,163,716 A | 12/2000 | Edwards et al. | |
| 6,216,027 B1 | 4/2001 | Willis et al. | |
| 6,226,543 B1 | 5/2001 | Gilboa et al. | |
| 6,241,724 B1 | 6/2001 | Fleischman et al. | |
| 6,271,834 B1 | 8/2001 | May et al. | |
| 6,428,487 B1 * | 8/2002 | Burdorff et al. | ........... 600/568 |
| 2001/0034530 A1 | 10/2001 | Malackowski et al. | |
| 2003/0050633 A1 * | 3/2003 | Ellman et al. | ............... 606/37 |

FOREIGN PATENT DOCUMENTS

WO   WO 00 10456   3/2000

OTHER PUBLICATIONS

Cardiac Pathways Corporation, Operator's Manual Realtime Position Management™ —Arrhythmia Mapping System Model 8100/8200/8300—Software Version 4.0.
Cardiac Pathways Corporation, Operator's Manual Realtime Position Management™ —Arrhythmia Mapping System Model 8100/8200/8300—Software Version 4.0, Jul. 28, 1997.

* cited by examiner

*Primary Examiner*—Lee S. Cohen
(74) *Attorney, Agent, or Firm*—Vista IP Law Group LLP

(57) ABSTRACT

A medical device for use by an operator to perform a medical procedure in a body includes a handle to be held by the operator, a shaft attached to the handle and an actuating assembly to control functions associated with the medical procedure. The shaft includes an operative distal portion to perform a medical procedure in the body. The medical device may be part of an ablation catheter system that is programmed to correlate one or more functions with the actuation of the actuating assembly. Multiple actuating assemblies may be provided. Each actuating assembly may be a button. Other types of actuating assemblies may also be used, such as switches or a trackball. The actuating assembly may also be provided on a sleeve that may be selectively attached to the handle of the catheter or the physician operating the catheter, for example.

46 Claims, 16 Drawing Sheets

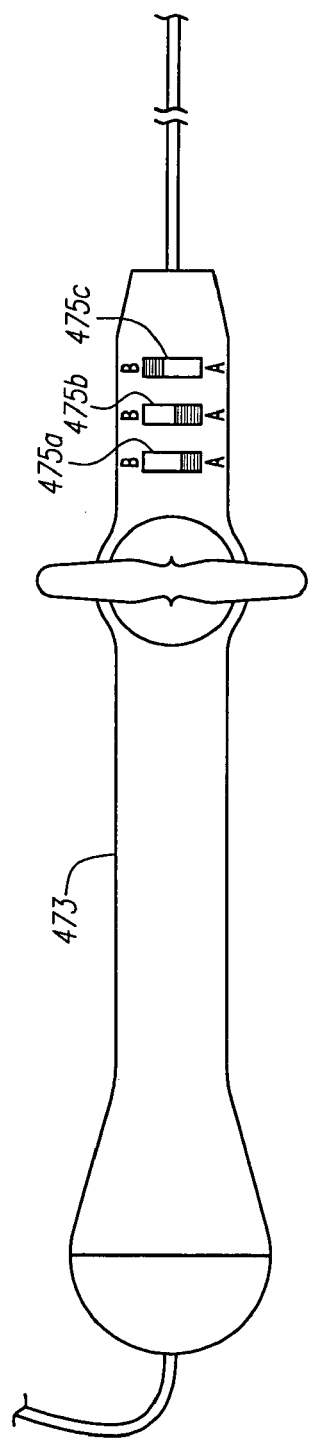
*FIG. 9A*
*FIG. 9C*
*FIG. 9B*

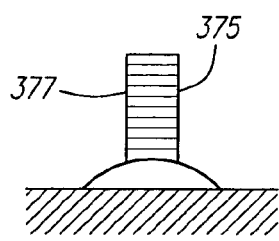
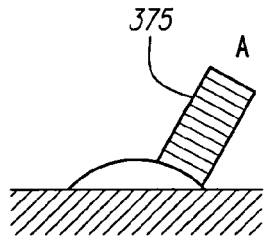
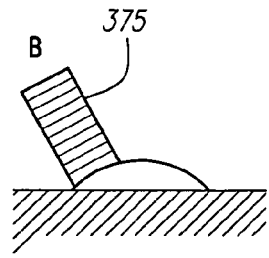
FIG. 10A     FIG. 10B     FIG. 10C
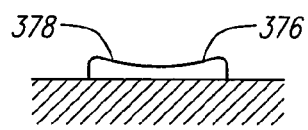
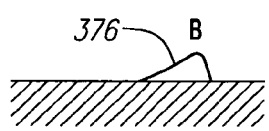
FIG. 11A     FIG. 11B     FIG. 11C
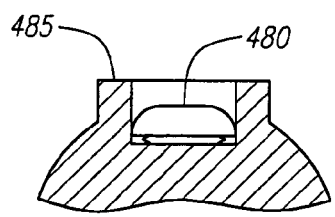
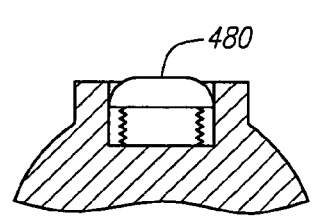
FIG. 12A        FIG. 12B

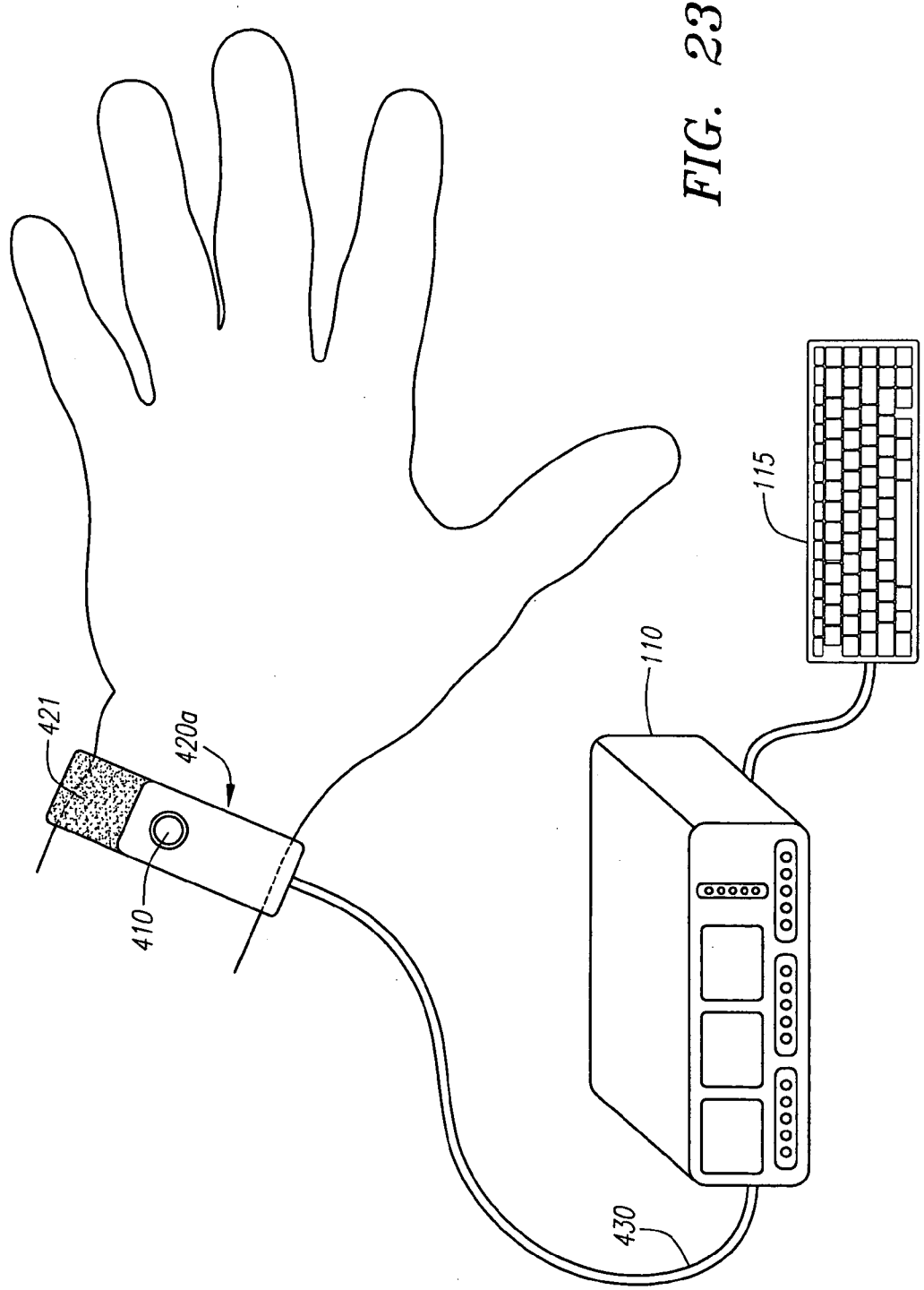

MEDICAL DEVICE CONTROL SYSTEMS

FIELD OF THE INVENTION

The present invention relates to medical devices, and more particularly, to control systems for medical devices.

BACKGROUND OF THE INVENTION

Catheters are often used in medical procedures to provide access to remote locations within a patient. A catheter can be inserted into the patient's body through a small incision and threaded through a blood vessel or other narrow passageway to reach the intended location. Dilatation catheters have been used to open blockages in blood vessels in percutaneous transluminal coronary angioplasty procedures, for example. Various types of catheters are also used in electrophysiology therapies to locate and treat cardiac arrhythmias. For example, one or more catheters may be used to pace, map and ablate cardiac tissue to block the passage of aberrant electrical signals.

Steering mechanisms have been developed to facilitate the transit of catheters through body lumens such as the vascular system. These mechanisms typically require that a physician or other trained medical professional hold and rotate the catheter to navigate the twists and branches of the body lumen. Movement of the steering assembly bends or deflects a distal portion of the catheter, allowing the physician to steer the catheter through the body lumen. In many applications, the ability to steer the catheter is critical to the success of the diagnostic or therapeutic protocol and may affect the risk of trauma to the patient as well. Moreover, the ability to precisely steer the catheter impacts the speed and ease by which the physician can properly position the distal portion of the catheter. Steering mechanisms are described in U.S. Pat. No. 6,163,716, which is incorporated by reference, herein, for example. Steering mechanisms are also described in U.S. Pat. No. 6,064,902, which is also incorporated by reference herein. Steering mechanisms have also been developed to control a catheter once it reaches its final destination. For example, steering mechanisms can be used to precisely position a catheter within the chambers of the patient's heart.

In a typical cardiac ablation procedure, electrical signals are applied to the cardiac tissue by a pacing catheter to induce arrythmia. A mapping catheter is then used to locate aberrant electrical pathways and currents emanating within the heart. The mapping catheter records the actuation times, the distribution and the waveforms of the electrical charges or potentials that trigger the pumping action of the heart muscle. The mapping catheter may be a "basket" catheter with a mapping basket at its distal end. The basket may comprise eight arms constructed of ribbons of a shape memory material, such as Nitinol. Each arm carries a plurality of mapping electrodes that detect the electrical activity of underlying cardiac tissue. A plurality of ultrasound receiving transducers are also mounted to each arm. Pacing and mapping catheters are described in U.S. Pat. No. 6,216,027 B1, for example, which is incorporated by reference herein.

After the aberrant electrical signals and pathways are located, lesions are formed in the cardiac tissue by an ablation catheter, to block the propagation of the aberrant electrical signals. The ablation catheter includes one or more energy transmitting elements, such as electrodes of gold, tantalum or platinum, to transmit energy, such as RF energy, to ablate the tissue to form the lesions. Ablation catheters are described in U.S. Pat. No. 6,241,724 B1, U.S. Pat. No. 6,216,027 B1, and U.S. Pat. No. 6,004,269, for example, which are assigned to the assignee of the present invention and are incorporated by reference herein. Two or more functions (pacing, mapping and/or ablation) may be provided on the same catheter, as described in U.S. Pat. No. 6,163,716, which is incorporated by reference herein.

Cardiac ablation systems typically include an imaging system to display the position of the one or more catheters used in the procedure. Ultrasound, magnetic, x-ray, or other imaging techniques known in the art may be used.

Cardiac Pathways Corporation, Sunnyvale, Calif., provides an Arrythmia Mapping System with Realtime Position Management™ Tracking Technology that enables the user to record, view and analyze intracardiac electrogram and EKG signals, as well as to view a realtime graphic representation of the catheters being used in the procedure. The views of the catheters may be rotated in three dimensions. A "time of flight" principle is used in combination with geometrical triangulation to establish a three-dimensional coordinate system using reference ultrasonic transducers on one or more reference catheters. Other catheters used in the procedure, such as the ablation catheter, include transducers to detect the ultrasound signals emitted by the reference transducers. Once the coordinate system is established, the three-dimensional location of the other catheters may be established by using the time of flight method to determine the distance between the catheter and the reference catheters. The coordinates of the catheter may then be established by basic algebra and the law of cosines, through triangulation. Operation of the Cardiac Pathways Arrythmia Mapping System is described in more detail in U.S. Pat. No. 6,216,027 B1, which is incorporated by reference herein. Cardiac Pathways Corporation has merged with Boston Scientific EP Technologies, Inc. San Jose, Calif.

It is often desirable to identify and store information concerning the procedure and the areas of the patient's heart that had been ablated or are currently being ablated. This information can include certain characteristics of the ablation procedure such as the temperature of the ablation electrode during the ablation procedure and the type of lesions that are formed. The date of the procedure may be recorded, as well. Some advanced ablation systems, such as the Cardiac Pathways system described above, are capable of identifying and storing this information.

Some ablation systems have the capability to color code certain information about a procedure. For example, cardiac tissue ablated in prior procedures may be identified by one color, such as yellow, while cardiac tissue ablated in the current procedure may be identified by a second color, such as green. In this way, the physician can readily distinguish between current ablation sites and earlier ablation sites. Likewise, the physician can assign color based on the power of the electrodes during the ablation process and is then capable of distinguishing between these ablation areas based on the color. The use of several colors may also assist the physician in his performance of an ablation procedure. For example, the use of two colors contrasts the different procedures. This can assist the physician by ensuring that the ablation areas of two different ablation procedures at least partially coincide with each other when such result is desired.

One drawback of conventional catheters, including catheters used in ablation procedures, is that they may require both of the physician's hands to hold the catheter and manipulate the steering assembly. In electrophysiology procedures, the initiation and completion of the pacing, mapping and ablation procedures, as well as color coding, for example, require input to a control device by an input device, such as a keyboard. Since the physician does not have a free hand to operate the keyboard or other such input device, the physician must verbally instruct others to operate the input device to initiate and complete these and other functions. Verbal instructions may be misunderstood and, in some instances, may be hard to communicate. In addition, there is a time delay between the giving of the verbal instruction and the performance of the request. At least one extra person may be required in the operating room to carry out the physician's instructions, increasing the costs of the procedure and increasing the likelihood of error.

Certain prior art ablation catheters include a handle with one or more buttons to control the powering up and powering down of an RF generator to provide energy to the one or more electrodes near the distal end of the catheter. See, for example, U.S. Pat. No. 6,142,994, which is incorporated by reference, herein. These buttons provide the physician with the ability to directly initiate ablation of cardiac tissue while holding the catheter. Other functions are not directly controlled by the physician conducting the ablation procedure, but by an assistant operating an input device, as discussed above.

SUMMARY OF THE INVENTION

It would be advantageous to enable a physician operating a medical device, such as an ablation catheter, to directly control other functions of the physician's choosing, as well.

In accordance with one embodiment of the invention, a system for performing a medical procedure comprises a device having a holding portion, a shaft associated with the holding portion and an actuating assembly proximal to the holding portion. The shaft has a distal portion that is operable to perform a medical procedure. A user programmable processing device is coupled to the actuating assembly. The processing device is programmable by the user, such as the physician, to initiate at least one of a plurality of functions in response to actuation of the actuating assembly. The actuating assembly may comprise a button, a switch, a trackball, a joystick, a disk, a sliding element or a rotatable sleeve, for example. One actuating assembly can control multiple functions. Multiple actuating assemblies may also be provided to control multiple functions. By providing the actuating assembly proximate the holding portion, a physician can steer and/or otherwise manipulate the catheter while initiating these other functions. The catheter system may also be programmed to initiate one of set predetermined functions in sequence in response to each actuation of the assembly.

Another aspect of the invention relates to a removable actuating assembly that is capable of attachment to the handle of a catheter, other objects close to the physician or to the physician's body. The removable actuating assembly can also be used with a catheter without buttons to add functionality to the catheter system.

Another aspect of the invention relates to the use of an actuating assembly near the catheter handle to navigate and select from a list or menu of options displayed on a visual display. Examples of suitable actuating assemblies include a push button assembly, a rotating or sliding disk or lever, and a pointing or navigation device. The visual display provides the physician with a plurality of options that the physician can select and perform by actuating one or more of the actuating assemblies near the catheter handle. For example, a menu or list of options can be displayed to the physician and, through the actuating of the actuating assembly, the physician can select and/or initiate one of the displayed options.

In another aspect of the invention, a system for conducting a medical procedure is programmed to respond to the manner in which an actuating assembly on the handle of the catheter is actuated. For example, the catheter system can initiate a first function with a response to a single triggering of the actuating assembly and may initiate a second, different function in response to a quick, repetitive triggering of the actuating assembly.

BRIEF DESCRIPTION OF THE DRAWINGS

FIGS. 9A-9C are cross sectional representations of a catheter handle having three rotatable switches as actuating assemblies.

FIGS. 10A-10C are three cross sectional representations of a rotatable switch having a relaxed position.

FIGS. 11A-11C are three cross sectional representations of another rotatable switch having a relaxed position.

FIGS. 12A-12B are two cross sectional representations of a two position button assembly.

FIGS. 21-23 are perspective views of removably attachable button assemblies attached to various parts of the catheter and/or physician.

DETAILED DESCRIPTION OF THE PREFERRED EMBODIMENTS

Figure 1:
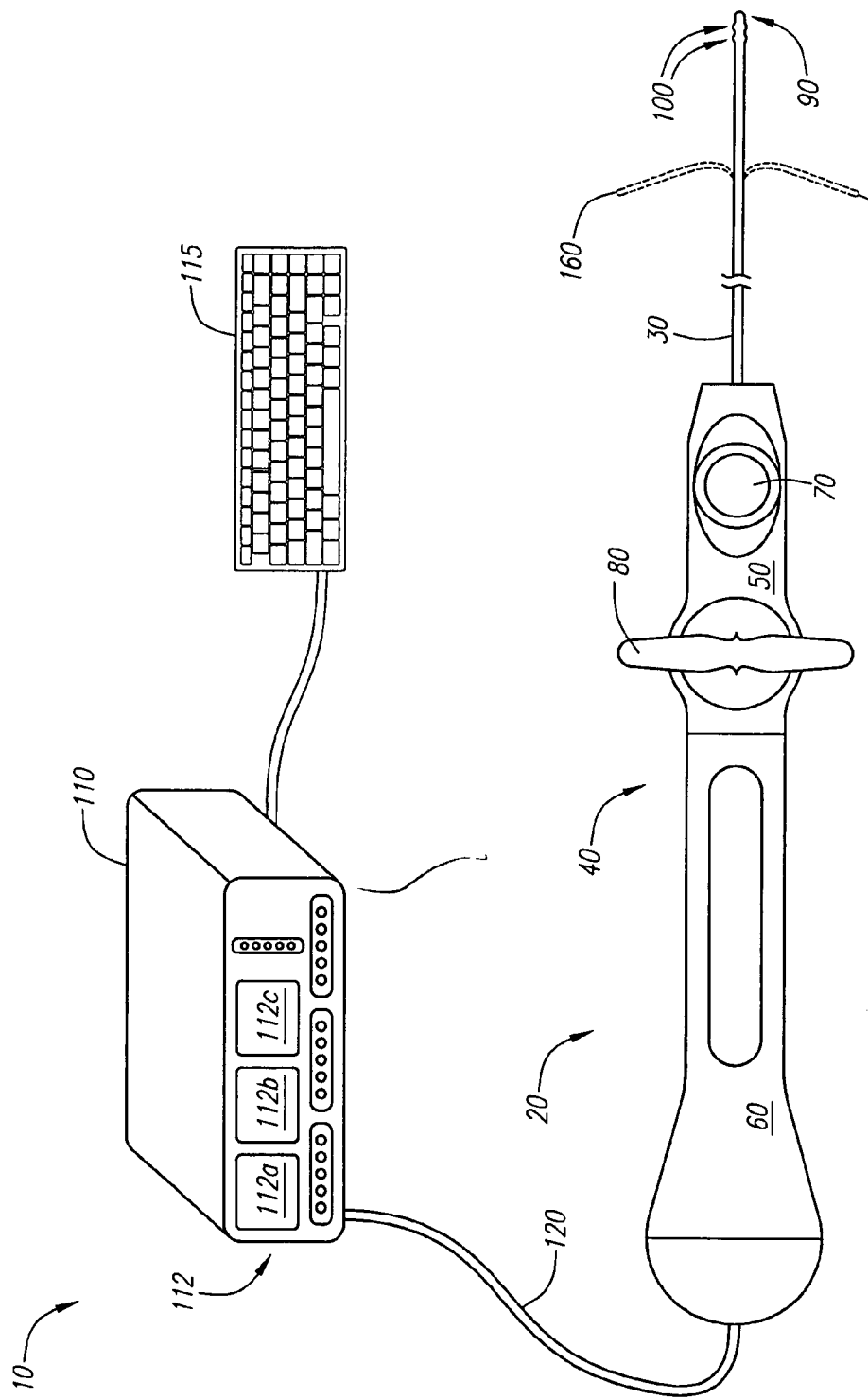
FIG. 1 is a perspective view of an ablation catheter system including a push button assembly on a catheter handle according to an embodiment of the present invention.

FIG. 1 illustrates an embodiment of a push button ablation catheter system 10 in accordance with an embodiment of the present invention. The system 10 includes a catheter 20 having a catheter body or shaft 30 and a catheter handle 40. The catheter handle 40 has a distal portion 50, a proximal portion 60, an actuating assembly 70, and a steering assembly 80. The actuating assembly 70 in this embodiment is a push button assembly 70 enabling a physician manipulating the catheter 20 to also directly control other functions of the system, as discussed further below.

The steering assembly 80 is used to control a distal portion 90 of the catheter body 30 as it is guided through the body's vascular system. The steering assembly 80 is attached to steering wires that extend through an interior lumen of the catheter handle 40 and the catheter body 30. The steering wires are secured to circumferentially spaced elements of the distal portion 90 of the catheter body 30 such that rotation of the steering assembly 80 to the right or left causes corresponding right or left deflection of the distal portion 90. In an alternative embodiment, the steering mechanism may be a unidirectional steering mechanism with a single steering wire that connects with the distal portion 90 for deflection of the distal portion 90 in only one direction. Steering mechanisms are described in more detail in U.S. Pat. No. 6,163,716, for example, which is incorporated by reference herein. Steering mechanisms are also described in U.S. Pat. No. 6,064,902, for example, which is also incorporated by reference, herein.

The ablation catheter system 10 includes an ultrasound imaging and control system 110, such as the Arrythmia Mapping System with Realtime Position Management ™ Tracking Technology, available from Cardiac Pathways Corporation, Sunnyvale, Calif. The imaging and control system 110 enables the user to record, view and analyze intracardiac electrogram and EKG signals, as well as to view a real-time graphic representation of the catheters being used, as discussed above. Operation of the Cardiac Pathways Arrythmia Mapping System is described in more detail in U.S. Pat. No. 6,216,027 B1, assigned to the assignee of the present invention and incorporated by reference herein. The imaging and control system 110 comprises an RF generator, a computer or other processing device, and memory or other storage device. Alternatively, the processing device and the storage device can be one or more separate units. As discussed above and in U.S. Pat. No. 6,216,027 B1, the imaging and control system 110 receives signals from a plurality of ultrasound transducers carried by reference catheters (not shown) located within the interior lumen or on the catheter body 30. A connector 120 electrically couples the catheter 20 and its components to the control and imaging system 110. Real time cross-sectional images of a patient's vasculature are generated and displayed on one more visual displays 112 of the control and imaging system 110, based on signals received from the transducers and processed by the processing device. The transducers may also be used to locate the catheter 20 within a patient's body and display the location of the catheter 20 as an image on the visual display 112. A physician can thereby determine the position of the distal portion 90 and the electrodes 100 relative to the cardiac tissue in real time on the imaging and control system 110. This information can be stored in the memory so that the physician can reposition the distal portion 90 of the catheter 20 at the stored location at a later time.

The Cardiac Pathways system includes three displays 112a-112c. One of the displays 112a is a Monitor Window, which displays up to 16 user-selected signals, such as EKG signals, in real time. Another of the displays 112b is a Tracking Window, which displays a real-time graphical representation of the reference catheters and one or more other catheters, such as an ablation catheter. The past position of a catheter can also be displayed. The third display 112c is a Review Window, which displays signals from the Monitor Window 112a for measurement, annotation and comparison.

Another example of a system capable of identifying a location of a catheter within a patient's body using ultrasound is described in U.S. Pat. No. 5,131,397, which is also assigned to the assignee of the present invention and is incorporated by reference herein.

The catheter 20 contains a plurality of electrodes 100 for mapping and/or ablating cardiac tissue. The electrodes 100 are powered via the generator of the imaging and control system 110. The imaging and control system 110 may also process electrical mapping signals picked up from the electrodes 100 and/or supply RF energy to the electrodes 100 for ablating cardiac tissue. Similar ultrasound/electrophysiology catheters are described in U.S. Pat. No. 6,241,724 B1, U.S. Pat. No. 6,216,027 B1, U.S. Pat. No. 6,163,716, and U.S. Pat. No. 6,004,269, for example, which are incorporated by reference herein.

Also included in the catheter system 10 is an input device 115, such as a keyboard or mouse, for programming the catheter system 10 and for controlling certain functions of the catheter system 10. These functions may include the powering up of the RF generator to supply energy to one or more of the electrodes 100 for ablating cardiac tissue, for example. In accordance with the invention, the input device 115 may also be used by the physician to preprogram the catheter system 10 before a procedure so that the system 10 will perform a predetermined function in response to an actuation of the push button assembly 70, as discussed further below.

During use of the catheter system 10, a physician positions the distal portion 90 of the catheter 20 by using the steering assembly 80 to maneuver the catheter body 30 through the vascular system to the heart. Left rotation of the steering assembly 80 causes the distal portion 90 to bend to the left to position 160, for example, and right rotation of the steering assembly 80 causes the distal portion 90 to bend to the right to position 170, for example. While maneuvering around turns and bends, the physician can observe the progress of the distal portion 90 on the Tracking Window 112c of the display 112b.

Figure 2:
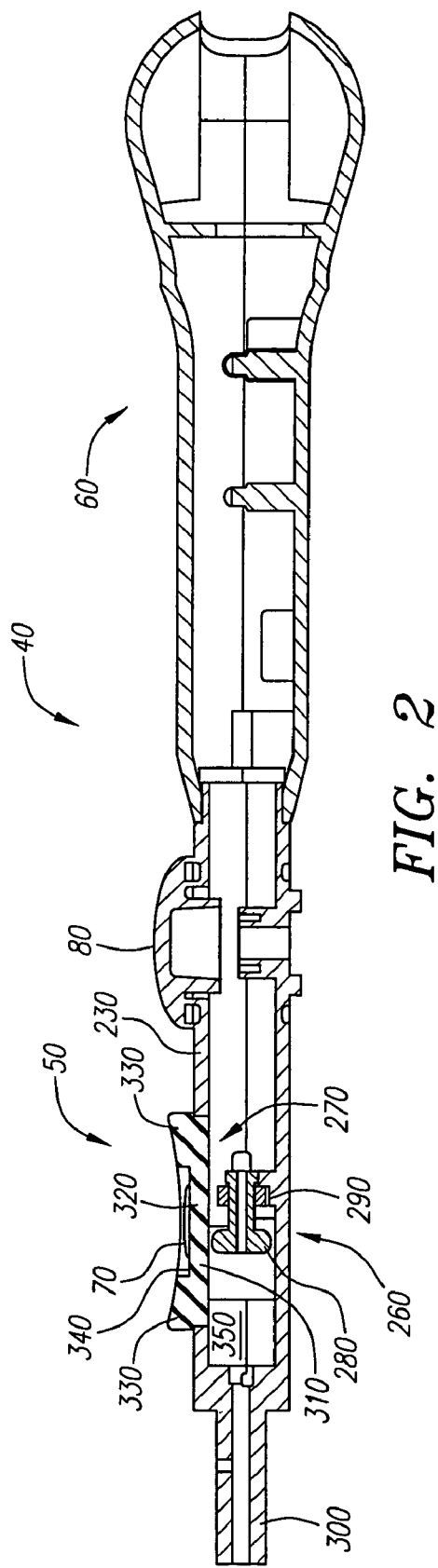
FIG. 2 is a cross-sectional representation of a catheter handle with a single push button assembly.

FIG. 2 is a cross-sectional side view of the handle 40, showing a generally flat top section 230 that carries the steering assembly 80 and the push button assembly 70. The push button assembly 70 is electrically connected to the control system 10 via the connector 120. In the alternative, the push button assembly 70 can be coupled to the control system 110 by an RF transmitter and receiver or by other means known in the art.

Preferably, the push button assembly 70 is secured to the flat top section 230 on the distal portion 50 of the handle 40, directly above a tension screw assembly 260. Attaching the push button assembly 70 above the tension screw assembly 260 may be cost efficient because a recess 270 to receive the push button 70 may be easily created by removing a transparent window (not shown), which is commonly secured to the flat top section 230 above the tension screw assembly 260. This location is also convenient for operation of the push button assembly 70 with the physician's thumb, regardless of which hand the physician uses to hold the catheter handle 40. Alternatively, the push button assembly 70 can be housed at any number of alternative locations along the handle 40, such as on the proximal portion 60 of the handle 40, on a side of the handle 40, or circumferentially opposite the steering assembly 80.

The tension screw assembly 260 includes a tension adjustment screw 280 and a tension adjustment hex nut 290. Adjustment of the tension screw assembly 260 permits fine-tuning of the tension of the distal end 90 of catheter 20 during assembly. The transparent window covers the tension adjustment screw 280 and the tension adjustment nut 290. The transparent window and recess 270 may be oval-shaped, or may, alternatively, be any number of other shapes, such as rectangular, circular or square, for example.

Figure 3:
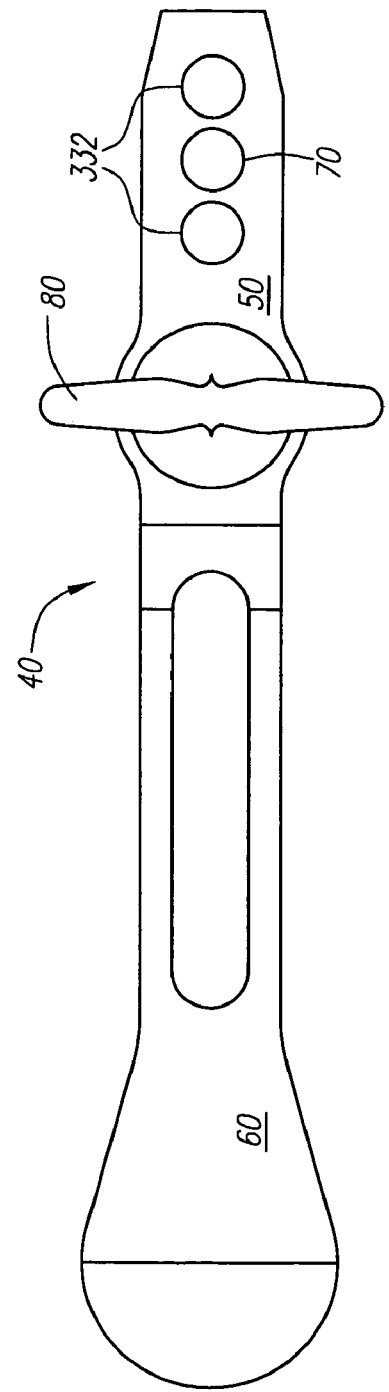
FIG. 3 is a top view of a catheter handle with push button assembly surrounded by protrusions to prevent accidental triggering of the push button.

The transparent window may be replaced by a button backing 310 that is dimensioned to fit within the recess 270. The button backing 310 carries the push button assembly 70 and includes a base 320 surrounded by a pair of arcuate protective ridges 330. As best seen in FIG. 2, the push button assembly 70 is preferably recessed within arcuate protective ridges 330 to avoid being accidentally depressed by the physician during normal use of the handle 40 or when the handle is laid down with the button 70 face down against a flat surface. Alternatively, the resilient push button 70 may be surrounded by a plurality of hard, inflexible protective raised bumps 332, which are the functional equivalent of the protective ridges 330, as shown in FIG. 3.

Returning to FIG. 2, the button backing 310 further includes an aperture 340 dimensioned to allow passage of electrical leads 350, which electrically couple the push button 70 to the imaging and control system 110 or other procedure-related operative equipment adapted to carry out a procedure-related task by pressing the push button 70. In the illustrated embodiment, the aperture 340 is a vertical, circular passageway; however, in an alternative embodiment, the aperture may be angled to avoid unnecessary bending of the electrical leads 350.

One example of the push button assembly 70 is a membrane switch, such as a tactile switch. A tactile switch provides a positive snap action response to one's thumb or finger when depressed. The snap action response can be achieved through the use of stainless steel domes embedded in the membrane switch.

The push button assembly 70 is positioned to be readily accessible to the physician so that the physician can pay the necessary attention to holding and steering the catheter 20. The button assembly 70 also provides the physician with the capability of performing other procedure-related tasks. The imaging and control system 10 is programmable such that the actuation of the push button assembly 70 can initiate one or more functions or activities.

In one example, the imaging and control system 110 can be programmed to add an identification mark on the Tracking Window of the display 112 when the push button assembly 70 is pressed. The imaging and control system 110 preferably displays cross-sectional or three dimensional images of the catheter or catheters being used. An identification mark gives the physician the ability to identify particular areas of interest within the heart and vascular system. The particular areas of interest can be stored in the storage device for later retrieval and use. In another example of the invention, the imaging and control system 110 can be programmed to identify and store information concerning the relative location and position of the distal portion 90 of the catheter body 30 relative to the patient's body, when the button assembly 70 is depressed. These functions may be particularly helpful to a physician to discuss or identify areas of interest at a later time or to return to a particular location to perform a procedure in the future. In another example of the invention, the push button assembly 70 can be used to store images displayed on the imaging system 110 for later retrieval or for printing these images from an attached printer (not shown). Through the actuation of the push button assembly 70, stored images can be retrieved from the storage device for display on the visual display 112. These stored images can then be compared by the physician to real time images of the patient.

In another example, the imaging and control system 110 can be programmed to deliver a dose of drugs to the patient percutaneously through a lumen in the catheter 20 upon actuation of the assembly 70. In a similar manner, the push button 70 can control the release of a supply of saline or an anti-coagulation drug through the catheter body 30 to prevent blood clotting.

Other examples of functions or tasks that the imaging and control system 110 can be programmed to initiate through the actuation of the push button assembly 70 include measuring the heart rate and measuring of the time duration between portions of a single heart beat. These procedures are carried out by sensing the heart beat, processing the information through the imaging and control system 110, and displaying the result on the visual display 112.

Yet another example includes programming the imaging and control system 110 to modify images on the visual display 112 in response to actuating the push button assembly 70. For example, the system 10 may be programmed such that depression of the push button assembly 70 magnifies an image or a certain area of interest of an image displayed on the visual display 112, or displays an alternative view of real time images. The imaging and control system 110 can also be programmed such that depression of the push button assembly 70 causes toggling between several images or views or modifies the layout of images on the visual display 112.

Another example includes programming the imaging and control system 110 to display colors on the visual display 112. As discussed in more detail above, the use of colors can provide the physician with helpful information concerning areas of the patient's that have been ablated. Such information can include the location, date or time of the previous ablation as well as the certain other characteristics of the ablation, such as the lesion pattern and the arrhythmia type.

Other functions that can be controlled by the button assembly 70 include the selection of different settings of the RF generator. The button assembly 70 can be used to select the temperature, duration, and power settings of the generator, for example.

Figure 4:
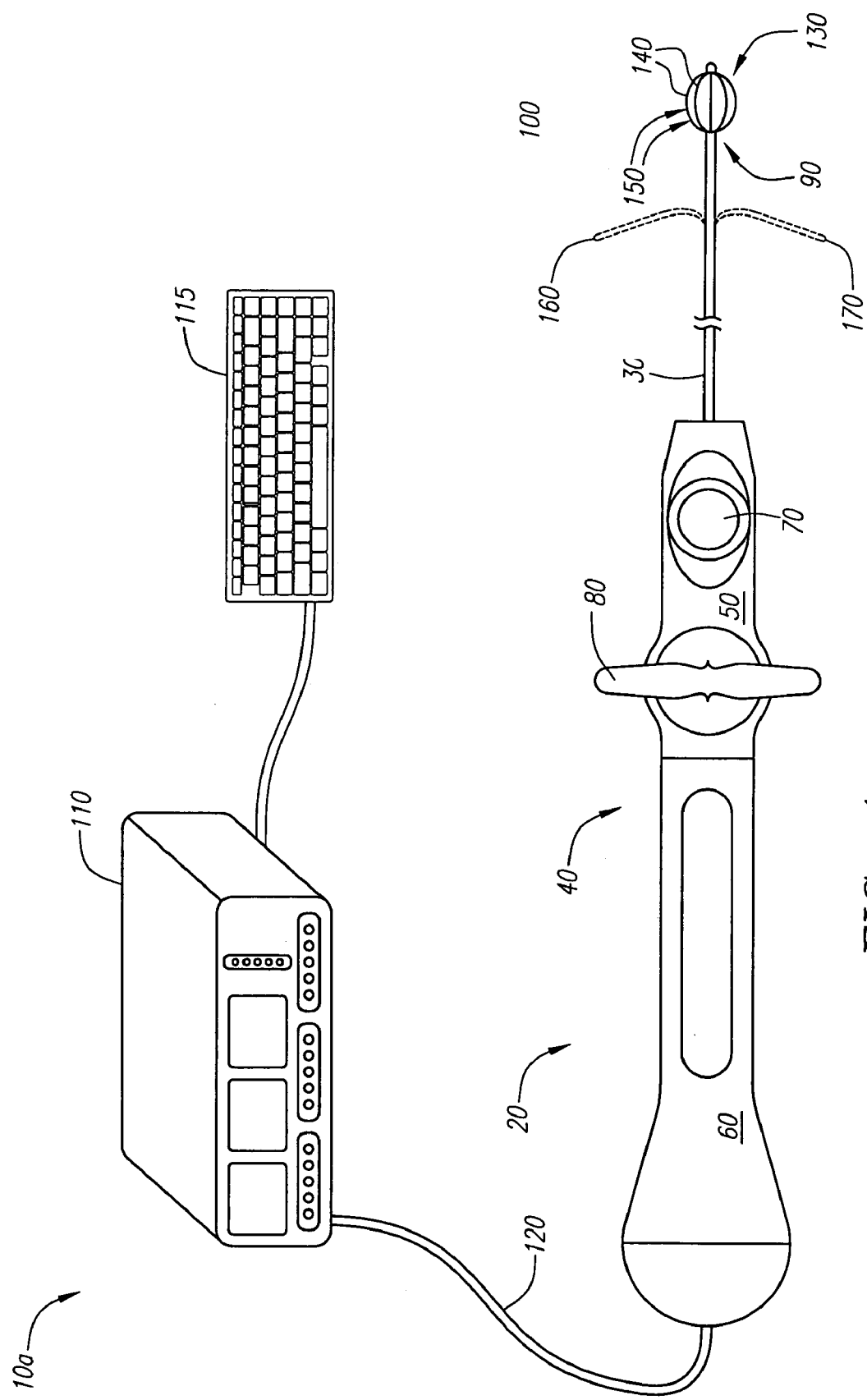
FIG. 4 is a perspective view of the catheter system similar to the system of FIG. 1, including an expandable basket on a distal end of the catheter.

In an ablation system 10a of FIG. 4, the distal portion 90 of the catheter 20 supports an expandable basket 130 with a plurality of splines 140. Each of the splines 140 carries one or more mapping electrodes 150. The imaging and control system 110 may be programmed so that the expandable basket 130 is deployed out of an opening in the distal portion 90 in response to a depression in the push button assembly 70. Such deployable electrode mapping assemblies are described in greater detail in U.S. Pat. No. 6,163,716, which is incorporated by reference herein. The system 110 can also be programmed to collapse the basket 130 in response to a depression of the same push button assembly 70.

In accordance with the invention, the system 10 may be programmed to associate any one of the functions described above, or other functions desired by the physician, through actuation of the button assembly 70. The system 10 may also be programmed to associate multiple functions with actuation of the button assembly 70, as desired by a physician.

One way a physician can control multiple functions of the catheter system 10 through the use of a push button assembly 70 is by varying the manner in which the push button assembly 70 is actuated. For example, the catheter system 10 can be programmed to perform one function (e.g. power up ablation electrodes) when the push button assembly 70 is pressed once and perform another function (e.g. power down ablation electrodes) when the push button assembly 70 is pressed twice within a short, predetermined time period. Alternatively, the imaging and control system 110 can be programmed to respond differently when it receives three quick presses of the button assembly 70 or one relatively long press.

In yet another alternative, the system 110 can be programmed to respond to a first press of the button assembly 70 by initiating a first programmed function and to a subsequent press of the button assembly 70 by stopping the programmed function. For example, a first press can power up the RF generator and a second press can power down the RF generator.

The catheter system 10 can also be programmed to respond to the release of a depressed button assembly 70 as well as the depression of the button assembly 70. The response to the release may be the opposite of the response to the depression. For example, if the catheter system 10 is programmed to respond to a depression of the button assembly 70 by powering up the RF generator 112 that supplies power to one or more ablating electrodes, the system 10 can also be programmed to respond to the release of the button assembly 70 by powering down the RF generator. In this way, the physician can control the duration of ablation by pressing and holding the button assembly 70 down.

Programming may be performed by a physician through the use of keyboard 115, or other input device, such as a mouse, prior to the start of the ablation procedure. Preferably, a graphical user interface ("GUI") is provided on the visual display 112 to facilitate the programming process. For example, the physician could choose from a list the available programmable functions displayed on the GUI and assign a corresponding manner in which the button assembly can be actuated to each of the desired functions by pointing and clicking a mouse.

The imaging and control system 110 can also be programmed to respond to a press of the button assembly 70 according to a predetermined sequence each time a physician actuates the push button assembly 70. For example, in a sequence useful for cardiac mapping and ablation, the system 10 can be programmed to respond as follows. After the physician navigates the distal end of the catheter 20 into the patient's heart, the physician actuates the push button assembly 70 a first time to initiate the pacing step of the procedure. In the pacing step, one or more of the electrodes 100 in the distal portion 90 sends an electric current into the cardiac tissue of a patient at a predetermined rate for a predetermined length of time. The electric current forces the patient's cardiac tissue into arrhythmia.

Pressing the push button assembly 70 a second time initiates the mapping step. During the mapping step, the catheter system 10 detects and processes electrical signals from the cardiac tissue. Signals may be analyzed to identify, among other things, a flutter in the cardiac tissue. The processed signals are displayed in a suitable format on the visual display 112 of the imaging and control system 110. In the Cardiac Pathways system, the signals may be displayed on the monitor window 112*a*. The trained physician can view the processed signals and navigate the distal portion 90 to a desired position in the heart for ablation.

A third press of the push button assembly 70 initiates the ablation step. The generator of the imaging and control system 110 then powers one or more of the electrodes 100 to be used to ablate the cardiac tissue. Energy delivery characteristics, such as the number of electrodes to be energized, the power and duration of the energy delivery, and/or the temperature of the electrodes during ablation, for example, can also be controlled by the user through the button assembly 70.

A fourth press of the button assembly 70 powers down the generator to stop the ablation step. A fifth press of the button assembly 70 initiates the mapping step again. A sixth press initiates the ablation step again. A seventh press powers down the generator. This process of mapping, ablating, and powering down recycles indefinitely with subsequent depressions of the button assembly 70 until a termination signal is received by the control system 110.

Two examples of termination signals include two quick presses of the button assembly 70 within a relatively short period of time and a single press and hold of the button assembly 70 for a relatively long period of time. The catheter system 10 may also be programmed to stop the programmed sequence in response to actuation of a separate actuator assembly located on the catheter handle 40. The use of multiple actuating assemblies is discussed further below. After the catheter system 10 receives the ending signal, the programmed sequence is reset to the beginning. The procedure can then be restarted from the beginning.

The following is another example of a programmable sequence that may be useful for mapping a heart using a catheter with basket assembly, as shown in FIG. 4. A first press of the button assembly 70 expands the basket 130 located near the distal portion 90 of the catheter body 30. The expandable basket 130 may be expanded within a chamber of the patient's heart. A second press of the button assembly 70 initiates the mapping step. The mapping electrodes 150 detect electrical signals, the signals are processed by the control system 110, and the result is displayed on the visual display 112. A third press of the button assembly 70 stops the mapping step and collapses the expandable basket 130. A fourth press expands the basket 130 again. This sequence is repeated until a termination signal is received. Just as with the previously described example of a programmable sequence, the catheter system 10 is programmed to stop the sequence upon receipt of a termination signal.

The catheter system 10 may also display the progress of a programmed sequence by listing all the steps of the programmed sequence on a display 112 and highlighting the current step in progress, for example. This provides the physician with information on the current status of the procedure and what to expect from the catheter system 10 the next time the push button assembly 70 is actuated.

The imaging and control system 110 can also be programmed to provide feedback to the physician concerning the current operation of the system 10 or the next function programmed to be initiated in response to actuation of the button assembly 70. In the case of ablation catheters, a signal may be provided to the physician that ablation electrodes at the distal portion 90 are currently powered up and ablating tissue. For example, the push button assembly 70 can vibrate when the ablation electrodes are powered. In the alternative, the catheter handle 40 may have a light that flashes when the ablation step is in progress. Alternatively, a signal can be provided to inform the physician of a potential risk if the button assembly 70 is actuated. For example, a light on the handle can flash when the catheter system 10 is in a state where the next press of the push button assembly 10 will power up the ablation electrodes. This signal can warn the physician so that the physician does not mistakenly press the button assembly 70 thinking that a different function will be carried out.

In the Cardiac Pathways system, various functions and displays are controllable by a physician's assistant by menus. In accordance with the invention, the menu driven features may be controlled with the push button assembly 70. This provides the physician with the ability to navigate and select features from a menu displayed on the visual display 112 of the imaging and control system 110.

Figure 5A:
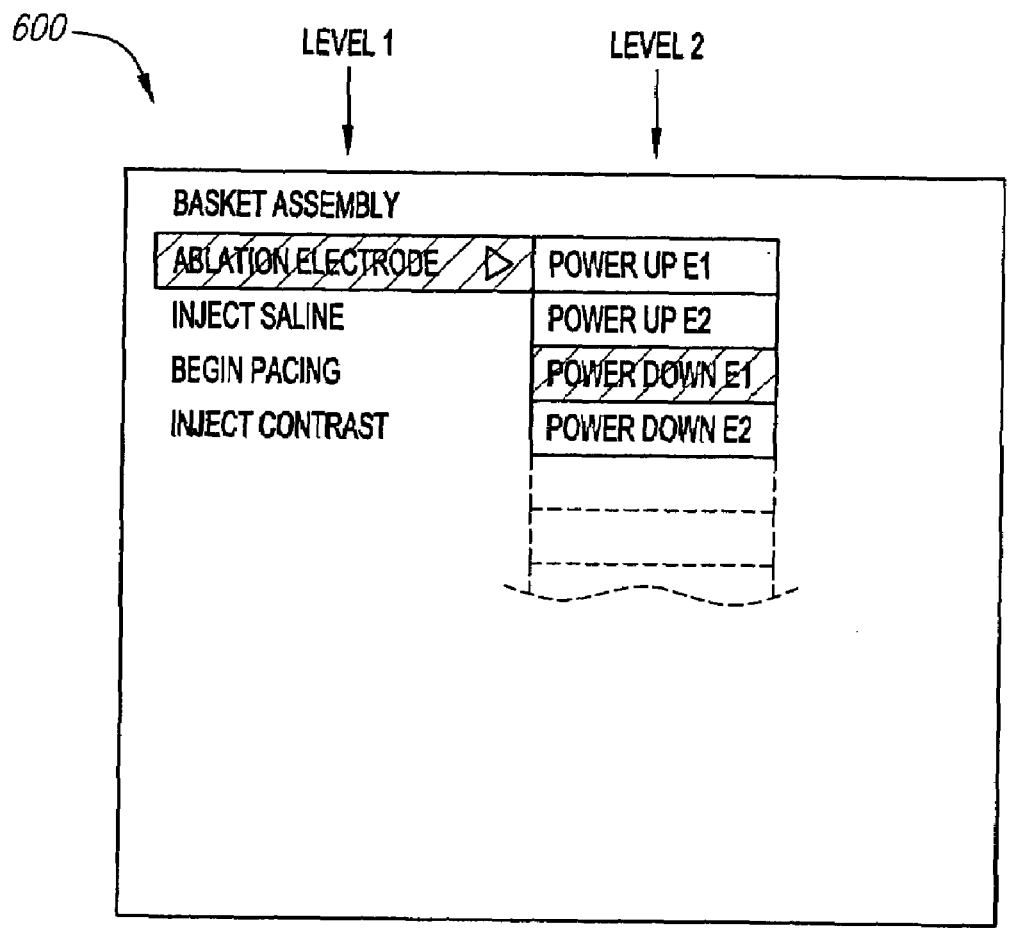
FIG. 5A is an example of a menu displayed on a visual display.
Figure 5B:
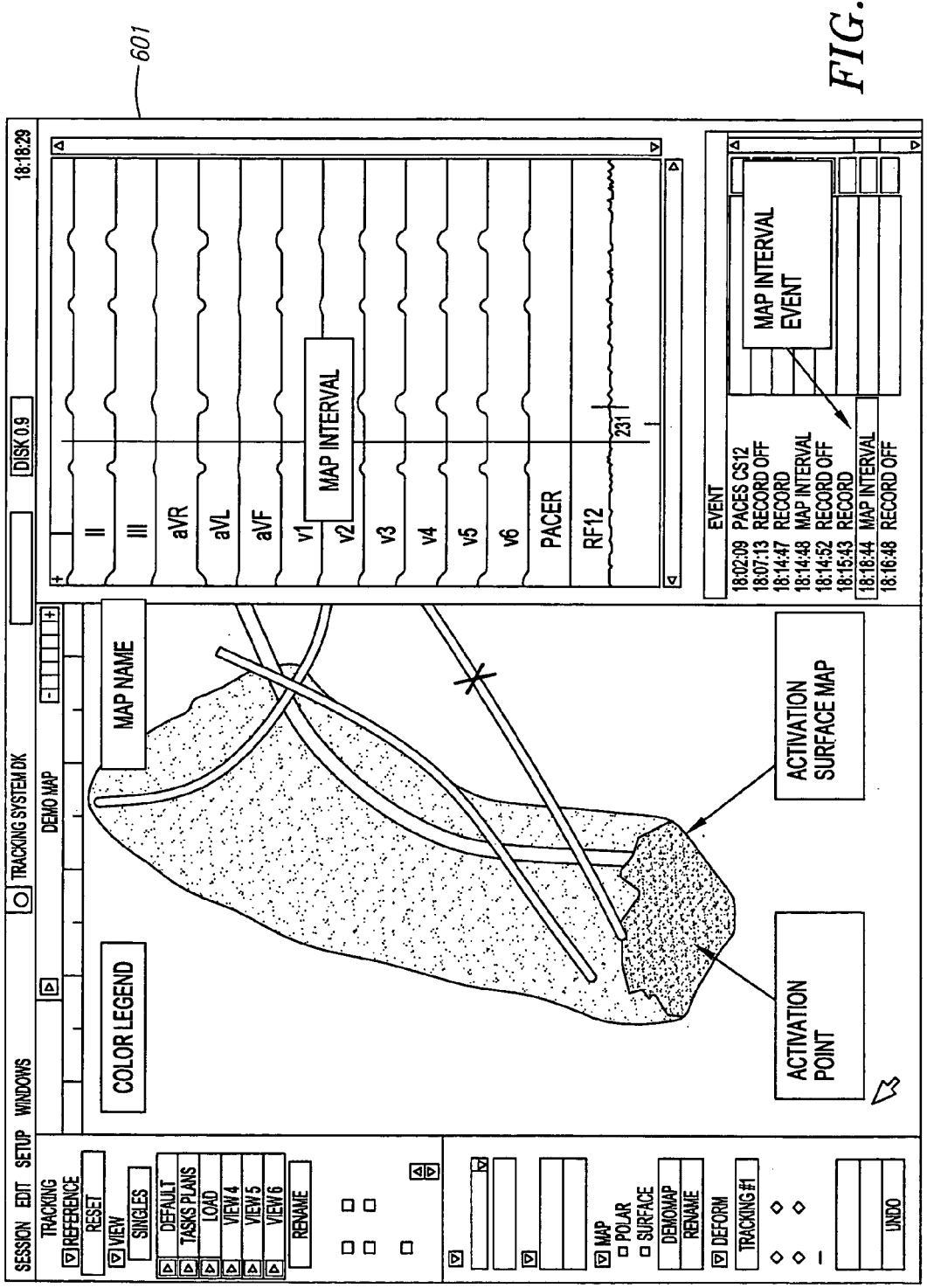
FIG. 5B is another example of a menu displayed on a visual display, where the menu is in the form of a tool bar.

FIGS. 5A-5B show two examples of menus that can be used in connection with the system 10. In the example of FIG. 5A, a menu 600 is shown as displayed on a visual display 112. The menu 600 contains a list of various functions that can be performed by the catheter system 10. In this example, the menu 600 is made of two levels, Level 1 and Level 2. As discussed in greater detail below, the physician has the ability to navigate through the menu 600 and select an operation by pressing the button assembly 70.

The menu 600 displays a list of first level options in Level 1. In this example, the Level 1 options include "basket assembly," "ablation electrode," and "begin pacing." The option "basket assembly" controls the deployment and collapse of a basket assembly at the distal portion 90. The option "ablation electrode" controls the powering of one or more ablation electrodes. The option "begin pacing" controls the application of electrical current to cardiac tissue to pace the heart. A single, quick depression of the button assembly 70 advances the current selection, which is highlighted, to the next available selection. In the example of FIG. 5A, if the selection "basket assembly" is highlighted, a single press of the button assembly 70 will highlight the selection "ablation electrode," as shown. A quick, double press of the push button 70 selects and may activate the highlighted selection. In some cases, a selection may bring up another set of options in Level 2. In the alternative, the list of options in Level 2 may be displayed automatically upon the highlighting of the Level 1 selection. In this example, a selection of "ablation electrode" brings up four options related to the powering up and powering down of two electrodes E1/E2 located on the distal portion 90 of the catheter body 30. As with the case of the options of Level 1, one of the options of Level 2 is highlighted. Navigation through the list in Level 2 is accomplished in the same manner.

FIG. 5B illustrates another exemplary depiction of a display screen of the imaging and control system 110. A toolbar 601 having various options related to the display of information is pictured on the left side of the display 112. In the center of the display 112 is a real time graphical representation of positions of reference and tracking catheters in the patient's heart. The upper right portion of the display is dedicated to the display of EKG signals received from mapping electrodes. These signals are useful for detecting arrhythmia and provides a physician with information to determine a suitable location of the patient's heart to ablate.

Navigation through the options of the toolbar 601 is achieved in a manner similar to the example of FIG. 5A. A single press of the push button assembly 70 advances through the list of highlightable selections, and a double click of the push button assembly 70 activates the selection. In the illustrated example, if the highlighted selection is "Reference," a single click will advance to the selection "View." A double click on the "View" selection will provide the physician with the capability of choosing from the list of options within the "View" subcategory. This list includes various options for operating the system and controlling the displayed view.

In the alternative, the catheter handle 40 may also have two actuators, one actuator for scrolling through the options and a second actuator for making the selection. The actuators may be buttons or switches, for example.

Figure 6A:
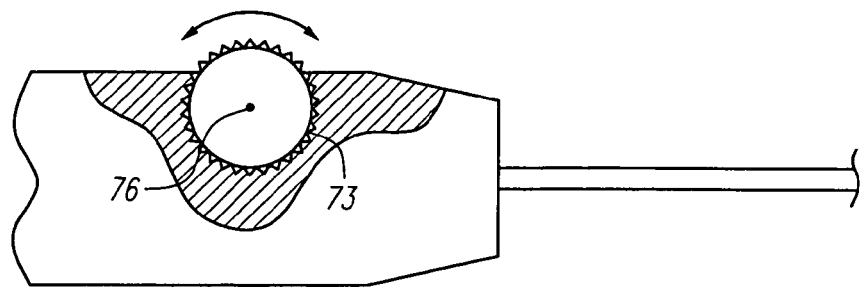
FIGS. 6A-6B are two partial views of a rotating scroll wheel having an additional actuation feature incorporated therein.
Figure 6B:
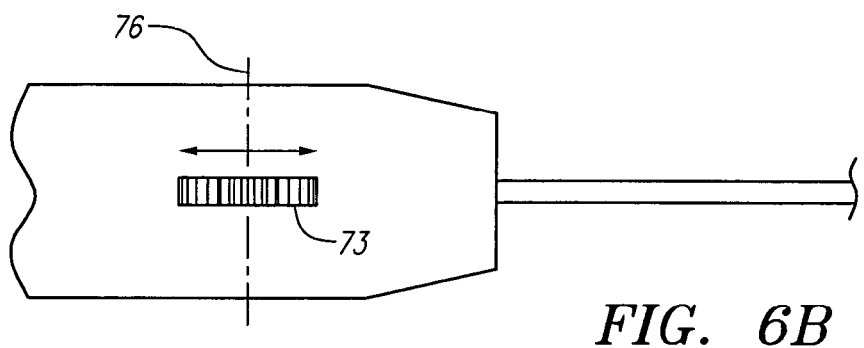
Figure 7A:
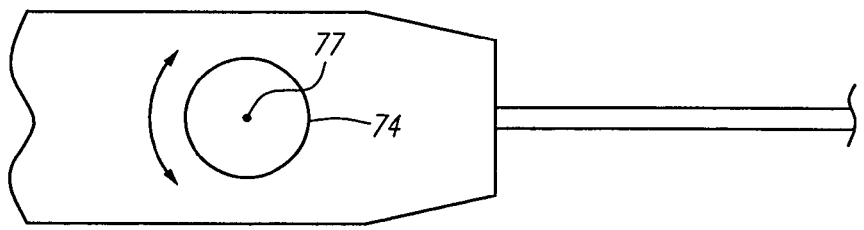
FIGS. 7A-7B are two partial views of a catheter handle having a rotatable disk as an actuating assembly.
Figure 7B:
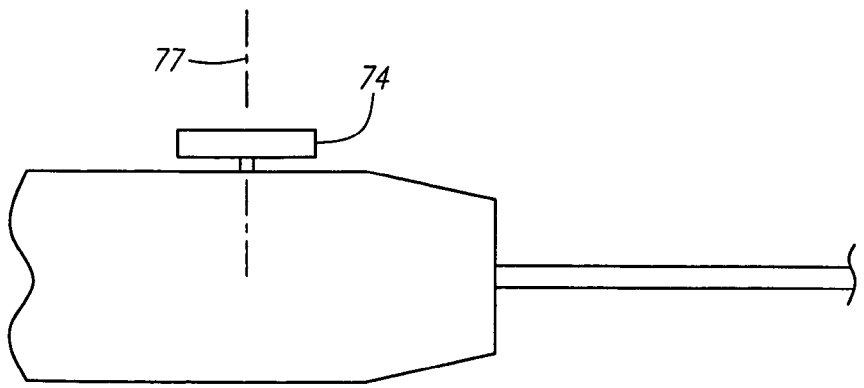

In an another alternative, the catheter handle 40 may have a rotating disk for scrolling through the listed options. The use of a rotating disk to navigate through a list of options may be preferable because it provides the physician with the capability of scrolling through the list of options in two directions, forward and backwards. FIGS. 6A-6B illustrate one example of a rotating disk 73, and FIGS. 7A-7B illustrate another example of a rotating disk 74. Both of the disks 73,74 rotate about an axis of rotation 76, 77, respectively.

Figure 8:
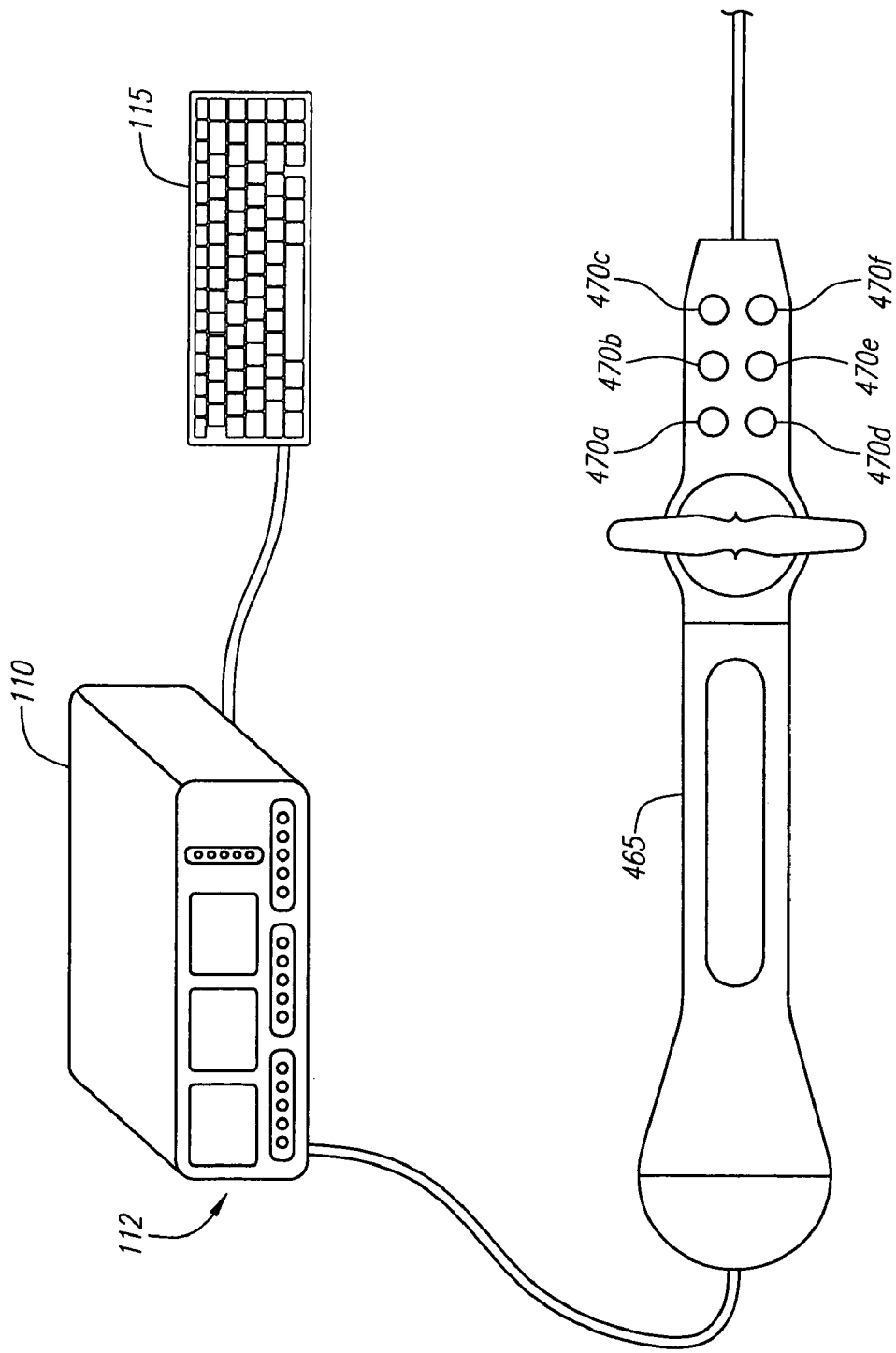
FIG. 8 is a perspective view of the catheter system having six actuating button assemblies.

Referring now to FIG. 8, in another embodiment of the invention, a catheter 465 has six buttons assemblies 470a-470f located near its holding portion. The button assemblies 470 are arranged in three rows of two pairs each, wherein each pair of button assemblies 470 controls different aspects of the operation of a particular function. For example, the imaging and control system 110 may be programmed so that the two button assemblies closest to the holding portion of the catheter 470a, 470d initiate the deployment and collapse of an expandable basket near the distal end of the catheter, respectively. Actuation of the two center button assemblies 470b, 470e may cause the commencement and completion of the sending of electrical pulses into the patient's tissue to pace the heart, respectively. The two button assemblies furthest from the handle portion 470c, 470f may initiate and stop the mapping step, respectively. While a preferred correlation of the buttons 470 is described, the buttons 470 can be programmed to control other functions and can be arranged in numerous alternative configurations, as well.

The button assemblies 470 may be embossed or otherwise marked with a distinctive symbol to provide the physician with information concerning the programmed function that is correlated with each of the buttons 470. In the alternative, the button assemblies 470 can be shaped to provide this information. The physician can be trained to associate a distinctive feature of the button assemblies with the programmed function or the programmed function can be obvious from the feature.

As mentioned above, switches may be provided instead of buttons. In FIGS. 9A-9C, a catheter 473 is provided with three switches 475a-475c instead of the six buttons of the embodiment of FIG. 8. Each of the switches 475 includes a protruding member 478, which is engageable and rotatable about an axis of rotation 479. The switches 475 have two positions, an A position and a B position. The switches are advanced from one position to the other by engaging the switches 475 with a thumb or finger and rotating the protruding portion 478 with respect to the axis of rotation 479.

The use of two position switches can be advantageous in certain applications. A single, double-position switch may provide the functionality of two button assemblies and thus may occupy less space on the handle of the catheter. Another benefit is that the operator can view the positions of the switches 475 to confirm that the system is in the intended configuration. As in the embodiment of FIG. 8, the imaging and control system 473 can be programmed to perform, or cease performance of, an operation in response to the position of the switches 475.

FIGS. 10A-10C and FIGS. 11A-11C illustrate two additional examples of switches 375, 376 suitable for use with a catheter. The switches 375, 376 are resilient in that they return to its original, relaxed position upon release. FIGS. 10A and 11A illustrate the switches 375, 376 in their relaxed position. Protruding portions 377, 378 of the switches 375, 376 are in its neutral position. The switches 375, 376 can be rotated by the physician about an axis to position A (illustrated in FIGS. 10B and 11B) or to position B (illustrated in FIGS. 10C and 11C). The physician can move the switches 375, 376 to position A to initiate one function of the catheter system and can move the switches 375, 376 to position B to initiate another function. In this way, the catheter assembly is capable of performing more than one function in response to actuation of one actuating device.

Alternatively, the switch 375, 376 can be sliding switches. The sliding switches 375, 376 are confined within slots and can be pushed by the physician along the slots in two directions. The switches can also return to a neutral or relaxed position upon release of the switches by the physician.

Referring now to FIGS. 12A-12B, two partial cross sectional representations of a double position button assembly 480 are shown in its depressed position and a released position, respectively. The button assembly 480 is capable of being locked in the depressed and released positions and toggles between the positions in response to pressure by the operator. As in the example of FIGS. 9A-9C, one double-position button assembly 480 can replace two single position button assemblies. Protrusions 485 preferably are shaped to surround the button assembly 480 to reduce the chance that an operator will inadvertently trigger a function of the catheter system.

Figure 13:
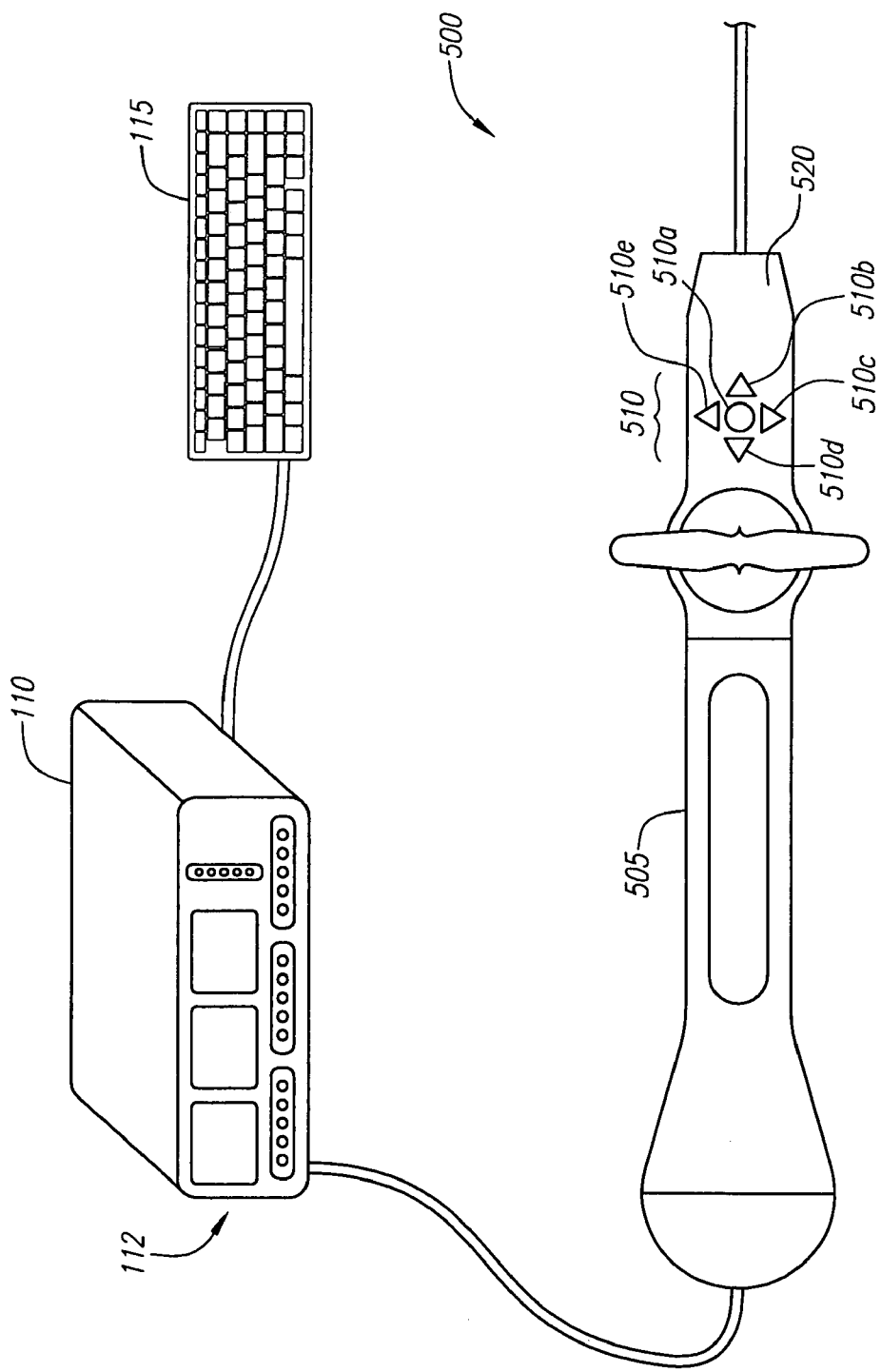
FIG. 13 is a cross sectional representation of catheter handle with five button assemblies in a 1-3-1 arrangement.

In an alternative embodiment illustrated in FIG. 13, a system 500 has a catheter 505 with five button assemblies 510a-510e located on a relatively flat portion of its handle 520. As in the example of FIG. 1, the system 500 provides option selection through the use of menus. The visual display 112 displays the menu or list of options to the physician. The physician navigates through, and selects options from, the menus through the button assemblies 510. More than one of the button assemblies 510 may be used to navigate through the menus. For example, the center button assembly 510e can be assigned to select an option and the remaining button assemblies 510a-510d can be assigned to scroll through each of the options.

Examples of other functions of the button assemblies 510 include the navigation of a pointer on one or more of the visual displays 112a-112c. One benefit of controlling a pointer is that it provides the physician with the ability to identify certain areas of interest of the patient's vascular system and magnify portions of images displayed on the visual display 112. The button assemblies 510 can also be used with a visual pointer to mark or highlight certain areas of interest on the visual display 112. These areas of interest may include, for example, blockage in the arteries of the patient, areas of the heart in which ablation procedures have already been performed, and precise locations on which the operator intends to perform a procedure. The imaging and control system 110 may be programmed to magnify the area of interest on the same visual display or on a separate visual display associated with system 110.

Figure 14A:
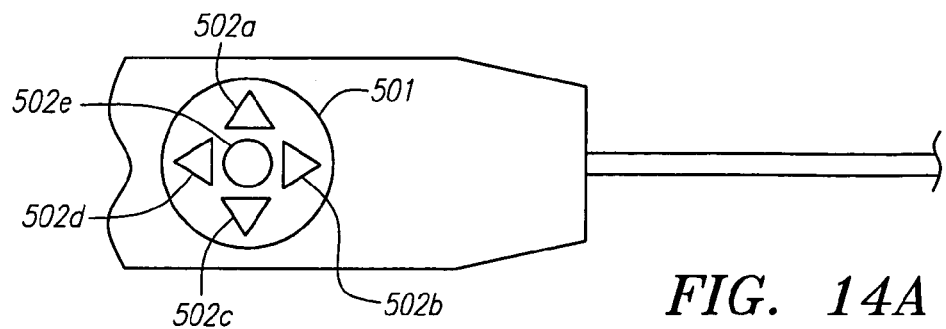
FIGS. 14A-14B are partial cross-sectional representations of a push button assembly having five depression areas.
Figure 14B:
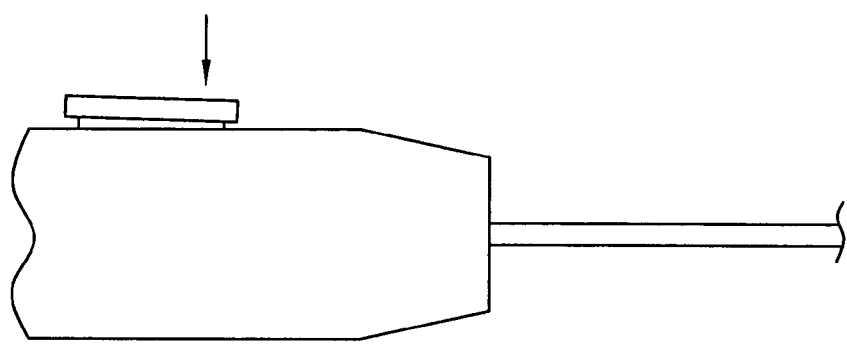
Figure 15:
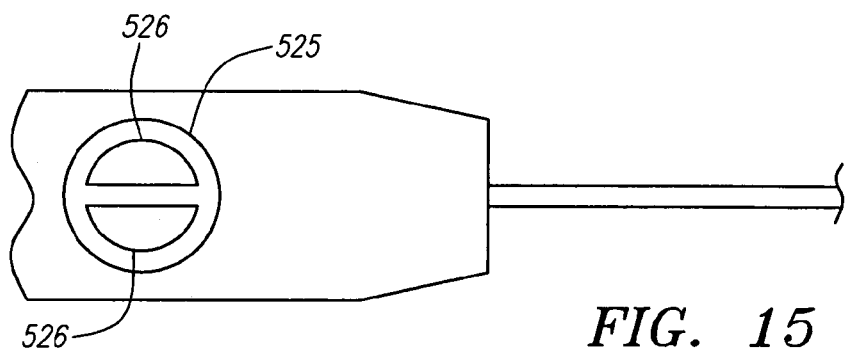
FIGS. 15-16 are two partial cross-sectional representation of alternative button assemblies having depression areas.
Figure 16:
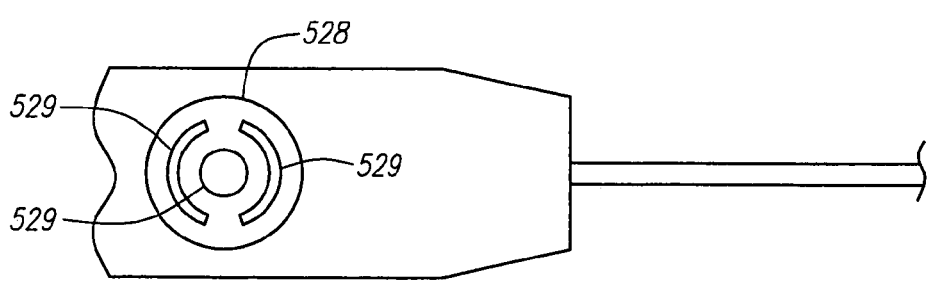

Referring now to FIGS. 14A-14B, in an embodiment similar to the embodiment of FIG. 13, a catheter handle has a button 501 shaped to have five recesses or depression areas 502a-502e. The button assembly 501 has the same functionality of the button assemblies 510 of FIG. 13. The button assembly 501 can be pressed by the physician in one of the five depression areas. 502a-502eInfrared sensors, pressure contacts or other types of sensors beneath the button 501 assembly are provided to detect depression of a particular area 502a-502e. Other examples of button assemblies are illustrated in FIGS. 15 and 16. The button assemblies 525, 528 each have depression areas 526, 529, respectively.

Figure 17A:
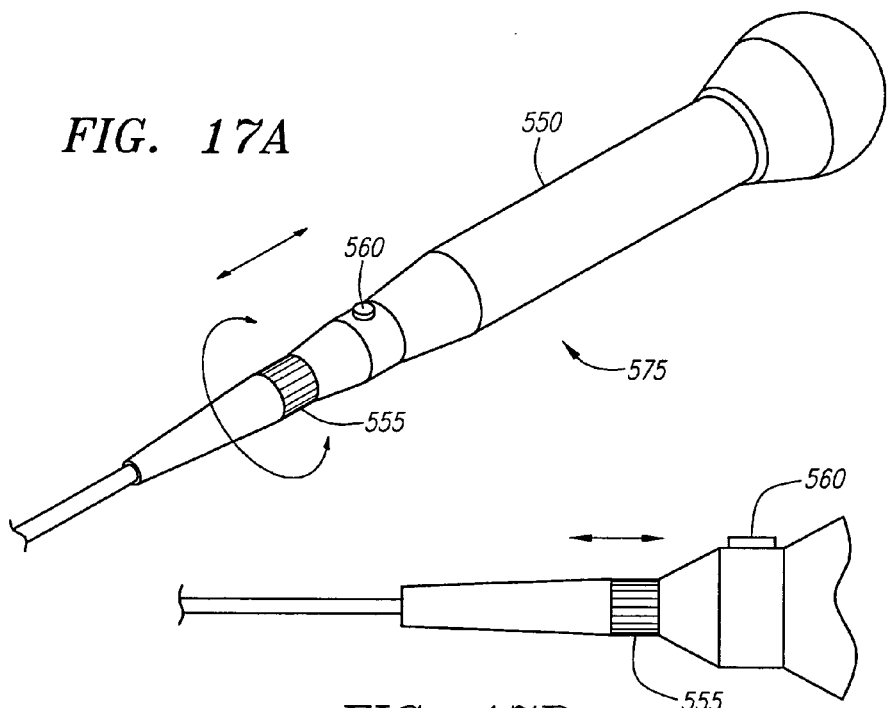
FIG. 17A is a perspective view of a catheter handle with a rotating sleeve.
Figure 17B:
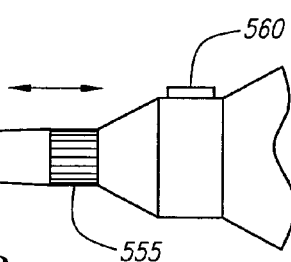
FIG. 17B is a partial cross-sectional representation of the rotating sleeve of FIG. 17A.

FIGS. 17A-17B illustrate another example of a catheter system 575 similar to the embodiment of FIG. 13. The system 575 includes a catheter 550 with a movable and rotatable sleeve 555. The rotatable sleeve 555 rotates around an axis in the axial direction of the catheter 550. The rotating aspect can be useful to navigate or scroll through menus displayed on an imaging system or display, as discussed above. The rotatable sleeve 555 is also capable of adjusting the magnification of images displayed on the visual display with the catheter system being programmed to increase the magnification when the sleeve 555 is rotated in one direction and decrease the magnification when rotated in the opposite direction. The rotating sleeve 555 is also movable in the axial direction. The axial movement of the sleeve 555 provides a second dimension to the capabilities of the catheter 550. The ability of the sleeve 555 to move in two dimensions provides the physician with the capability of navigating a pointer on the imaging system.

Figure 18A:
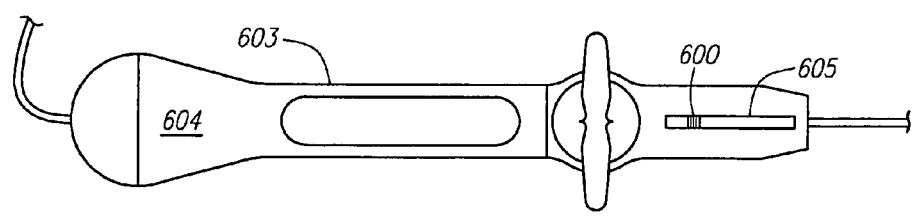
FIGS. 18A-18C are three cross-sectional representations of sliding element actuating assembly.
Figure 18B:
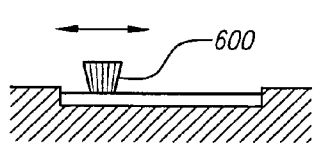
Figure 18C:
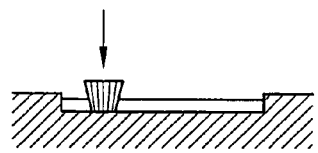

Additional examples of functional actuating assemblies that can be placed on a handle of the catheter are illustrated in FIGS. 18A-18B and FIGS. 19A-19B. FIGS. 18B-18C are cross sectional, schematic representations of a sliding element 600 that can be incorporated in a handle 603 of a catheter 604. The sliding element 600 is configured to slide along a linear recess 605. For example, the sliding element can control a 200 m function of the display of an image. The imaging and control system 110 may be programmed to initiate, terminate or modulate a function in response to the linear movement of the sliding element. For example, the sliding element 600 can control a zoom function of the display of an image to magnify and reduce the image. Optionally, the sliding element 600 can also be adapted to be pressed into the body of the handle 603, to add additional functionality.

Figure 19A:
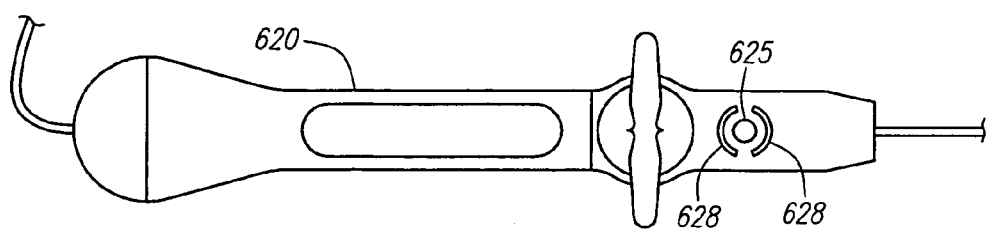
FIGS. 19A-19B are two views of a catheter handle having a miniature trackball to navigate and point.
Figure 19B:
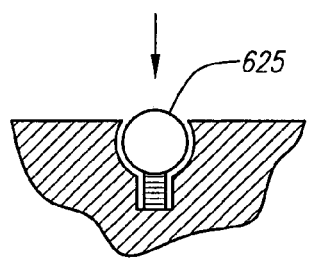

FIGS. 19A-19B illustrate another example of an actuation assembly. A catheter 620 includes a miniature trackball 625 embedded in its body. A physician can navigate through menus displayed on the visual display 112 or navigate a pointer on the visual display 112 by rolling the trackball 625, for example. The physician can also make a selection from the menu or can utilize other features of the catheter system by pressing the trackball 625 into the body of the catheter 620. Alternatively, the physician can actuate one of the two buttons assemblies 628. Sensors, such as light emitting diodes (not shown), can be incorporated within the handle to monitor the movement of the track ball 625.

Figure 20:
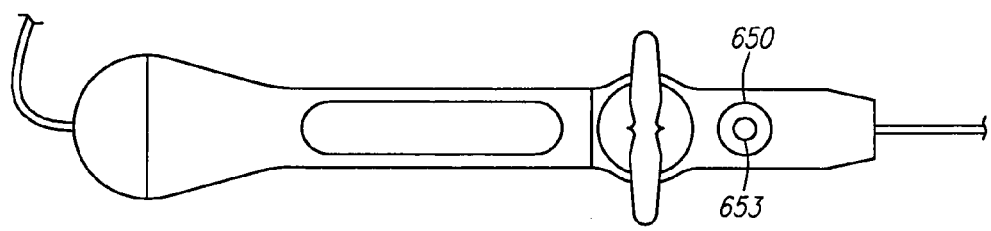
FIG. 20 is a cross-sectional representation of a catheter handle having a joystick pointing feature.

In another embodiment, FIG. 20 depicts a catheter handle having a pointing or navigation assembly 650. The pointing assembly 650 has pressure sensors for sensing the magnitude and direction of a force placed upon a contact portion 653 of the pointing assembly 650. The control and imaging system 110 is capable of processing signals received from the sensors to navigate a pointer on the visual display 112. The processing of the signals is accomplished in a manner similar to the eraser head, TrackPoint pointing apparatus found in the center of keyboards of many laptop computers. A more detailed explanation of an exemplary pointing device is described in U.S. Pat. No. 6,271,834, which is incorporated by reference herein.

Figure 21:
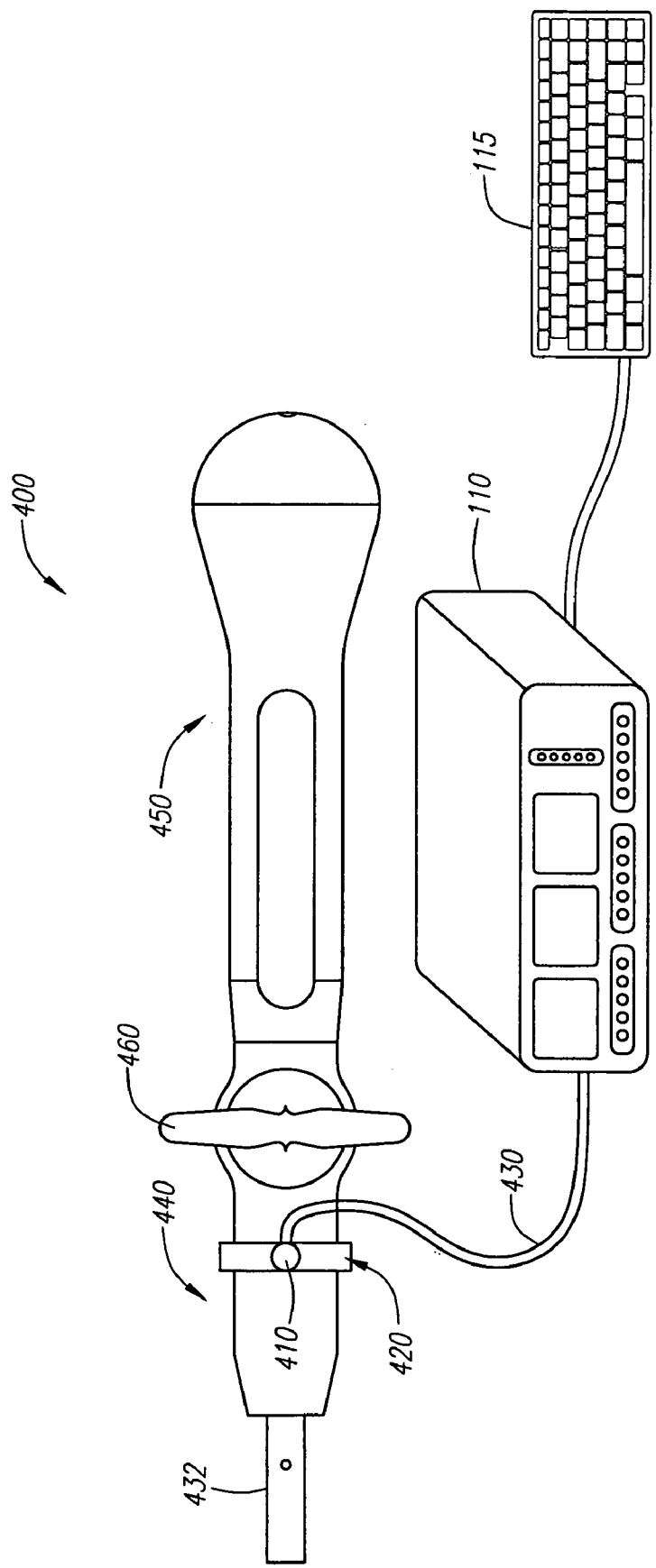

In accordance with another embodiment, a push button or other such actuating assembly may be removably attachable to a catheter handle 400 or the physician's wrist or finger. FIG. 21 shows a push button assembly 410 including a sleeve 420. Preferably, the sleeve 420 is elastic. Due to its elastic nature, the sleeve 420 can be attached at an infinite number of locations along the longitudinal axis of the catheter handle 400 by stretching it out and allowing it to contract around the handle 400 at a desired location. Electrical leads 430 couple the push button assembly 410 to the control and imaging system 110 or other procedure-related operative equipment adapted to carry out a procedure-related task by actuating the push button assembly 410. The push button assembly 410 preferably includes a membrane switch such as the tactile switch described above with respect to FIG. 1.

The sleeve 420 may be slid over a catheter body 432, and a distal portion 440 of the catheter handle 400, toward a proximal portion 450 of the catheter handle 400, for mounting the push button assembly 410 to the handle 400. Mounting the push button 410 just distal of a steering assembly 460, with the top of the push button 410 facing in the same direction as the top of the steering assembly 460, eases actuation of the push button assembly 410 by a physician's thumb, regardless of which hand the physician uses to hold the catheter handle 400.

Although the sleeve 420 is shown positioned around the distal portion 440 of the handle 400, in alternative embodiments, the sleeve 420 may be positioned in any number of locations along the handle 400, including around the proximal portion 450 of the handle 400. The sleeve member 420 can be made of any flexible material including, but not limited to, plastic, rubber or any elastomer.

Figure 22:
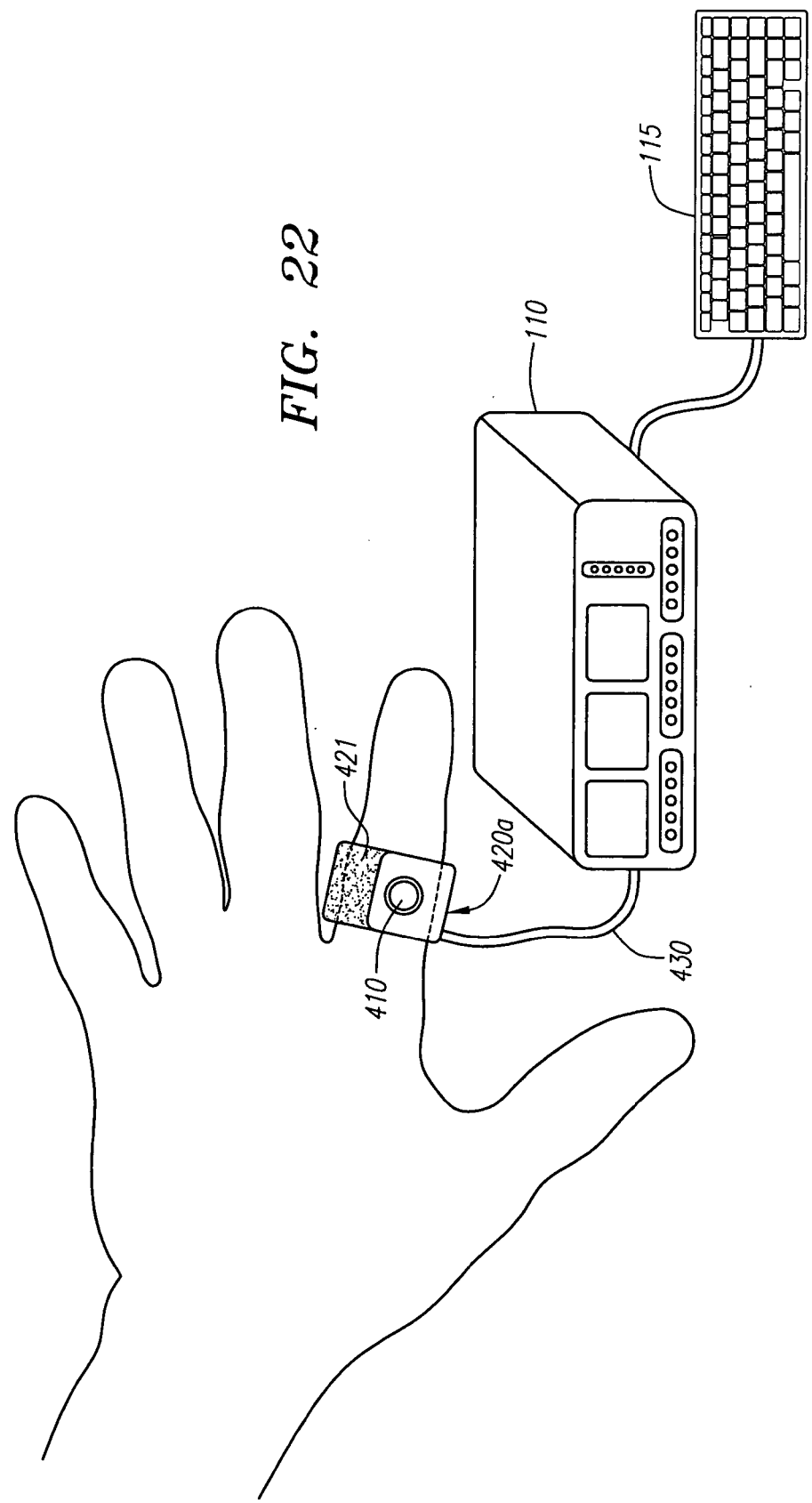

Alternatively, as shown in FIG. 22, a sleeve 420a can be a fabric material with VELCRO™ sections 421, i.e., a single strap with an opposing hook section and loop section at opposite ends, for simple attachment and detachment around the user's finger, for example. In FIG. 23, the sleeve 420a is shown attached to the operator's wrist. The sleeve 420a could also be attached to the handle 400 and the sleeve 420 of FIG. 21 could be attached to the operator, by suitable adjustment of the dimensions of the respective sleeve.

While the embodiments described above relate to catheters used in cardiac ablation systems, the invention may be incorporated in other types of catheters, as well. For example, a push button assembly may be provided on a dilatation catheter for performing angioplasty. The angioplasty system may be programmed to deploy a dilatation balloon near the distal portion of the catheter in response to a depression of the push button assembly and collapse the balloon in response to a subsequent depression of the button, for example. The system could also be programmed to deliver drugs upon depression of the button assembly.

Furthermore, while the invention is particularly useful with catheters having at least one steering mechanism for controlling a distal end of the catheter, the invention may be useful with non-steerable catheters, as well.

In addition, the invention may be used with catheters for ablation procedures in other parts of the body, such as in the remainder of the circulatory system, other soft tissue, such as the liver, the kidneys, the brain, the pancreas, the lungs, the prostate and in the soft tissue of the bones, for example.

The invention may also be used with laparoscopic probes which provide minimally invasive direct access for introducing ablation elements or other therapeutic or diagnostic devices at a distal end of the probe into interior body regions through body cavity walls. Functions of laparascopic probe systems can be user programmed and controlled in a similar manner as described above. In the specification and claims, the term "catheter" is meant to encompass hand held probes of any type, as well.

In addition, while the embodiments have been described with respect to the Cardiac Pathways Arrythmia Mapping System, other imaging and control systems may be used. For example, a fluoroscopic imaging system may be used, in which case, in addition to the functions described above, the actuating assembly may be used to inject contrast for improved visualization of the site of interest. Magnetic and x-ray based imaging systems can also be used.

Although the disclosed examples illustrate button assemblies in certain location on the handle, the invention is not specifically limited to those locations. Any type of actuatable device, including pointing and navigating devices may be provided, in any suitable location near the handle, as well.

It will evident to those skilled in the art that the invention is not limited to the details of the foregoing illustrative examples and that the present invention may be embodied in other specific forms without departing from the scope of the invention, which is defined by the following claims.

We claim:

1. A medical device, comprising:
a shaft having a distal end and a proximal end;
an operative element carried by said distal shaft end;
a handle carried by said proximal shaft end; and
an actuating element associated with said handle and configured for initiating a medical function; and
a user programmable processing device configured for allowing a user to define an association between said medical function and a specific manner in which said actuating element is actuated.

2. The medical device of claim 1, wherein said actuating element is configured for initiating a plurality of different medical functions, and wherein said processing device is configured for allowing a user to define an association between said plurality of medical functions and a specific manner in which said actuating element is actuated.

3. The medical device of claim 2, wherein said processing device is configured for allowing said user to associate a defined sequence of said plurality of medical functions with said actuating element, such that said plurality of medical functions is initiated in said sequence in response to said specific actuating manner.

4. The medical device of claim 3, wherein said specific actuating manner comprises repeatedly actuating said actuating element.

5. The medical device of claim 1, wherein said processing device is configured for allowing said user to define said medical function.

6. The medical device of claim 1, wherein said processing device is configured for allowing said user to define said specific actuating manner.

7. The medical device of claim 6, wherein said processing device is configured for allowing said user to define a number of actuations of said actuating element within a predetermined period of time.

8. The medical device of claim 6, wherein said processing device is configured for allowing said user to define a period of time in which said actuating element is actuated.

9. The medical device of claim 1, wherein said operative element is configured for being used in a performance of said medical function.

10. The medical device of claim 1, wherein said shaft is an intravascular catheter shaft.

11. The medical device of claim 1, wherein said processing device is coupled to said handle via an external cable.

12. A medical device, comprising:
a shaft having a distal end and a proximal end;
at least one operative element carried by said distal shaft end;
a handle carried by said proximal shaft end; and
an actuating element associated with said handle and configured for initiating a plurality of different medical functions in a predetermined sequence, wherein at least two of said plurality of medical functions are respectively initiated in response to at least two actuations of said actuating element.

13. The medical device of claim 12, wherein:
a first of said plurality of medical functions is configured for being initiated when pressure is applied to said actuating element;
said first function is configured for being terminated when said pressure is released from said actuating element;
a second of said plurality of medical functions is configured for being initiated when pressure is again applied to said actuating element; and
said second function is configured for being terminated when said pressure is again released from said actuating element.

14. The medical device of claim 12, wherein said at least one operative element comprises one or more electrodes, and said plurality of medical functions comprises delivering ablation energy to said one or more electrodes, and processing mapping signals received from said one or more electrodes.

15. The medical device of claim 12, wherein said at least one operative element comprises a mapping basket, said plurality of medical functions comprises expanding said mapping basket, mapping with said mapping basket, and collapsing said mapping basket.

16. The medical device of claim 12, further comprising another actuating element associated with said handle, said other actuating element terminating said sequence of functions when actuated in a specific manner.

17. The medical device of claim 12, further comprising a processor configured for presenting a list of said sequence of functions and highlighting a function that is currently being performed.

18. The medical device of claim 12, wherein one of said plurality of medical functions is a therapeutic function, and wherein said system is configured for providing a warning signal when said therapeutic function is next in said sequence.

19. The medical device of claim 18, wherein said therapeutic function comprises delivering ablation energy.

20. The medical device of claim 12, wherein said handle provides a user with feedback when said system commences each of said medical functions.

21. The medical device of claim 12, wherein said at least one operative element is configured for being used in a performance of said medical functions.

22. The medical device of claim 12, wherein said shaft is an intravascular catheter shaft.

23. A medical device, comprising:
a shaft having a distal end and a proximal end;
at least one operative element carried by said distal shaft end;
a handle carried by said proximal shaft end; and
an actuating element associated with said handle, wherein at least two different medical functions are assigned to said actuating element, such that said at least two different medical functions are individually initiated when said actuating element is respectively actuated in at least two different manners, wherein said at least two medical functions are in different categories.

24. The medical device of claim 23, wherein said actuating element has at least two positions and initiation of said at least two medical functions are respectively dependent on said at least two positions.

25. The medical device of claim 23, wherein said actuating element has a first relaxed position, a second unrelaxed position, and a third unrelaxed position, wherein said switch is biased towards said first position upon release of pressure placed on said switch, and said second position is one of said at least two different manners, and said third position is another of said at least two different manners.

26. The medical device of claim 23, wherein said first actuating manner comprises actuating said actuating element a first number of times within a defined period of time, and said second actuating manner comprises actuating said actuating element a second different number of times within said defined period of time.

27. The medical device of claim 23, wherein said first actuating manner comprises actuating said actuating element for a first defined period of time, and said second actuating manner comprises actuating said actuating element for a second different defined period of time.

28. The medical device of claim 23, wherein said at least one operative element is configured for being used in a performance of said at least two medical functions.

29. The medical device of claim 23, wherein said shaft is an intravascular catheter shaft.

30. A medical device, comprising:
a shaft having a distal end and a proximal end;
at least one operative element carried by said distal shaft end;
a handle carried by said proximal shaft end; and
an actuating element associated with said handle element and configured for initiating one of at least two different medical functions when actuated a first number of times within a defined period of time and initiating another of said at least two medical functions when actuated a second different number of times within said defined period of time.

31. The medical device of claim 30, wherein said first number of times is one time, and said second number of times is two times.

32. The medical device of claim 30, wherein said at least one operative element is configured for being used in a performance of said at least two medical functions.

33. The medical device of claim 30, wherein said shaft is an intravascular catheter shaft.

34. A medical device, comprising:
a shaft having a distal end and a proximal end;
an operative element carried by said distal shaft end;
a handle carried by said proximal shaft end; and
an actuating element associated with said handle and configured for initiating a function; and
a user programmable processing device configured for allowing a user to define a specific manner in which said actuating element is actuated to initiate said function.

35. The medical device of claim 34, wherein said processing device is configured for allowing said user to define a number of actuations of said actuating element within a predetermined period of time.

36. The medical device of claim 34, wherein said processing device is configured for allowing said user to define a period of time in which said actuating element is actuated.

37. The medical device of claim 34, wherein said operative element is configured for being used in a performance of said function.

38. The medical device of claim 34, wherein said processing device is coupled to said handle via an external cable.

39. A medical device, comprising:
a shaft having a distal end and a proximal end;
at least one operative element carried by said distal shaft end;
a handle carried by said proximal shaft end; and
an actuating element associated with said handle; and
a processing device configured for presenting a list of different medical functions, wherein said actuating element is configured for being actuated to advance through said medical function list and for being actuated to select initiation of one of said medical functions.

40. The medical device of claim 39, wherein said medical function list is divided into a plurality of categories.

41. The medical device of claim 39, wherein said actuating element is configured for advancing from one function in said medical function list to a subsequent function in said medical function list when actuated one time within a defined period of time, and configured for selecting a current function in said medical function list when actuated two times within said defined period of time.

42. The medical device of claim 39, wherein said at least one operative element is configured for being used in a performance of said medical function.

43. The medical device of claim 39, wherein said processing device is coupled to said handle via an external cable.

44. A medical device, comprising:
a shaft having a distal end and a proximal end;
at least one operative element carried by said distal shaft end;
a handle carried by said proximal shaft end; and
an actuating element associated with said handle, wherein said actuating element has at least two positions and at least two different medical functions are assigned to said actuating element, such that said at least two different medical functions are individually initiated when said actuating element is respectively placed in said at least two positions.

45. A medical device, comprising:
a shaft having a distal end and a proximal end;
at least one operative element carried by said distal shaft end;
a handle carried by said proximal shaft end; and
an actuating element associated with said handle, wherein said actuating element has a first relaxed position, a second unrelaxed position, and a third unrelaxed position, wherein said switch is biased towards said first position upon release of pressure placed on said switch, and wherein at least two different medical functions are assigned to said actuating element, such that one of said at least two different medical functions is initiated when said actuating element is placed in said second position, and another of said at least two different medical functions is initiated when said actuating element is placed in said third position.

46. A medical device, comprising:
an intravascular catheter shaft having a distal end and a proximal end;
at least one operative element carried by said distal shaft end;
a handle carried by said proximal shaft end; and
an actuating element associated with said handle, wherein at least two different medical functions are assigned to said actuating element, such that said at least two different medical functions are individually initiated when said actuating element is respectively actuated in at least two different manners.

* * * * *